(12) United States Patent
Pavlik et al.

(10) Patent No.: US 8,670,838 B2
(45) Date of Patent: Mar. 11, 2014

(54) RESISTANCE WELDED JUNCTION FOR MEDICAL ELECTRICAL LEADS

(75) Inventors: Daniel R. Pavlik, Ramsey, MN (US); Jordon D. Honeck, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 2823 days.

(21) Appl. No.: 10/717,721

(22) Filed: Nov. 20, 2003

(65) Prior Publication Data

US 2005/0113896 A1 May 26, 2005

(51) Int. Cl.
*A61N 1/02* (2006.01)
(52) U.S. Cl.
USPC ............................. 607/116; 607/119; 607/122
(58) Field of Classification Search
USPC ....................... 607/116, 122, 119; 219/121.64
See application file for complete search history.

(56) References Cited

U.S. PATENT DOCUMENTS

| | | | | |
|---|---|---|---|---|
| 4,214,804 A | | 7/1980 | Little | 339/183 |
| 4,413,636 A | | 11/1983 | Jasso | 128/786 |
| 5,385,578 A | * | 1/1995 | Bush et al. | 607/122 |
| 5,522,872 A | * | 6/1996 | Hoff | 607/119 |
| 5,676,694 A | | 10/1997 | Boser et al. | 607/122 |
| 5,935,159 A | | 8/1999 | Cross, Jr. et al. | 607/116 |
| 6,016,436 A | * | 1/2000 | Bischoff et al. | 600/374 |
| 6,249,708 B1 | * | 6/2001 | Nelson et al. | 607/122 |
| 6,373,024 B1 | | 4/2002 | Safarevich et al. | 219/121.64 |
| 6,643,550 B2 | * | 11/2003 | Westlund et al. | 607/37 |
| 6,912,423 B2 | * | 6/2005 | Ley et al. | 607/37 |
| 6,934,589 B2 | * | 8/2005 | Sundquist et al. | 607/122 |
| 2002/0147488 A1 | | 10/2002 | Doan et al. | 607/122 |

OTHER PUBLICATIONS

Quality Resistance Welding Solutions: Defining the Optimum Process, http://www.unitekequipment.com/res_product/pdf/OptWeldWeb.pdf.
Technical Application Brief, "High Frequency Inverter Feedback Modes," Nuggets, Unitek Equipment, vol. 1, No. 1 (Nov. 1997).
Technical Application Brief, "Electrode Force Control for Foot and Air Actuated Weld Heads," Nuggets, Unitek Equipment, vol. 2, No. 1 (May 1999).
Technical Application Brief, The Importance of Squeeze Time in Resistance Welding, Nuggets, Unitek Equipment, vol. 2, No. 2 (May 1999).
Technical Application Brief, "Welding Material Control," Nuggets, Unitek Equipment, vol. 2, No. 3 (Oct. 1999).

* cited by examiner

*Primary Examiner* — Tammie K Heller
(74) *Attorney, Agent, or Firm* — Reed A. Duthler; Stephen W. Bauer

(57) ABSTRACT

A medical electrical lead component includes a groove formed in a surface of the component. The medical electrical lead includes a portion of a conductor positioned within the groove and a resistance weld formed between the portion of the conductor positioned within the groove and the component. In one embodiment, the portion of the conductor positioned within the groove includes a pre-weld diameter greater than the depth of the groove.

14 Claims, 8 Drawing Sheets

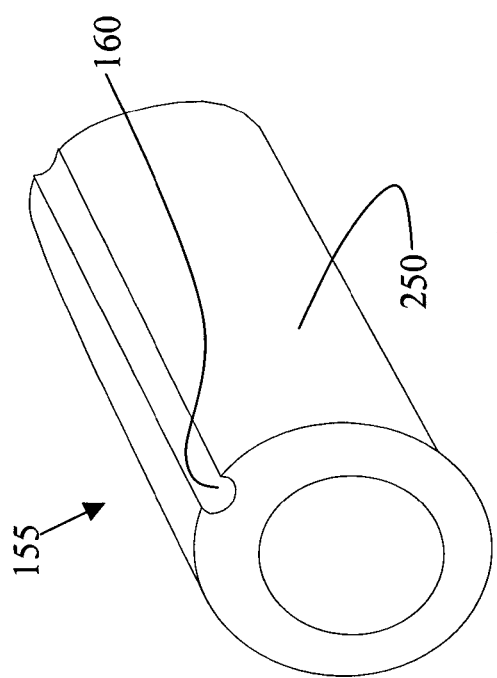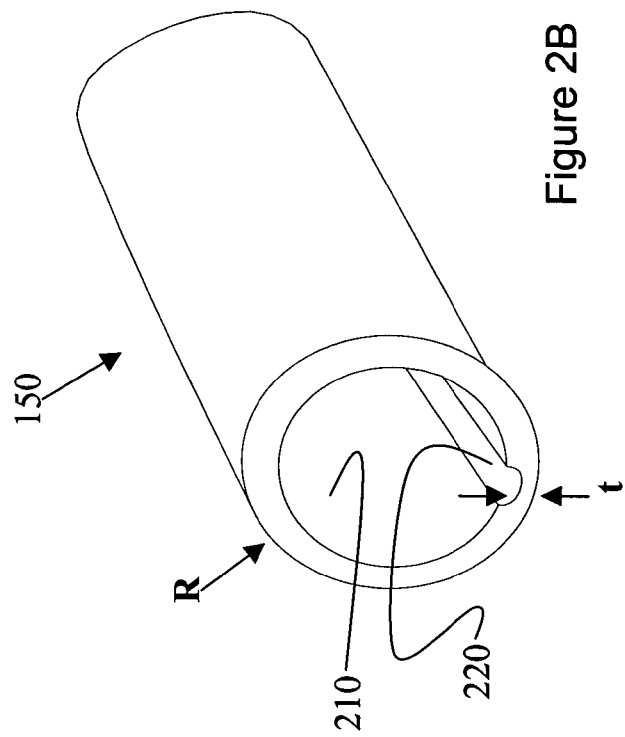
Figure 2A
Figure 2B

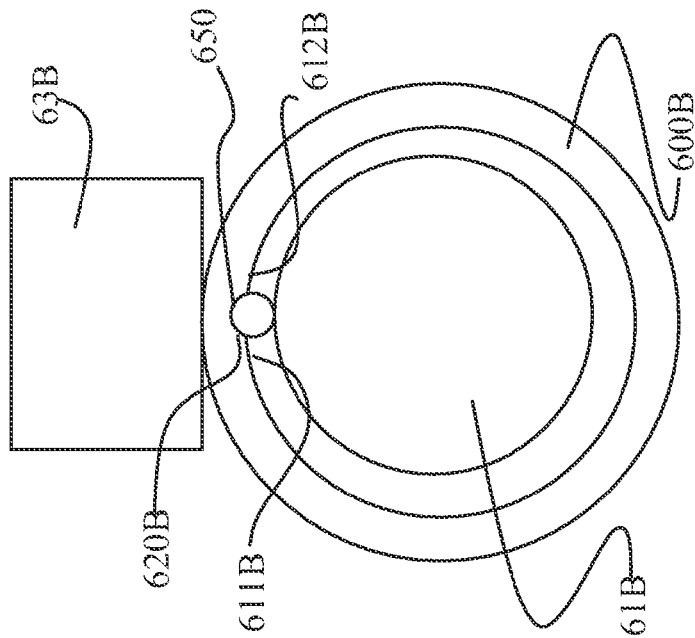
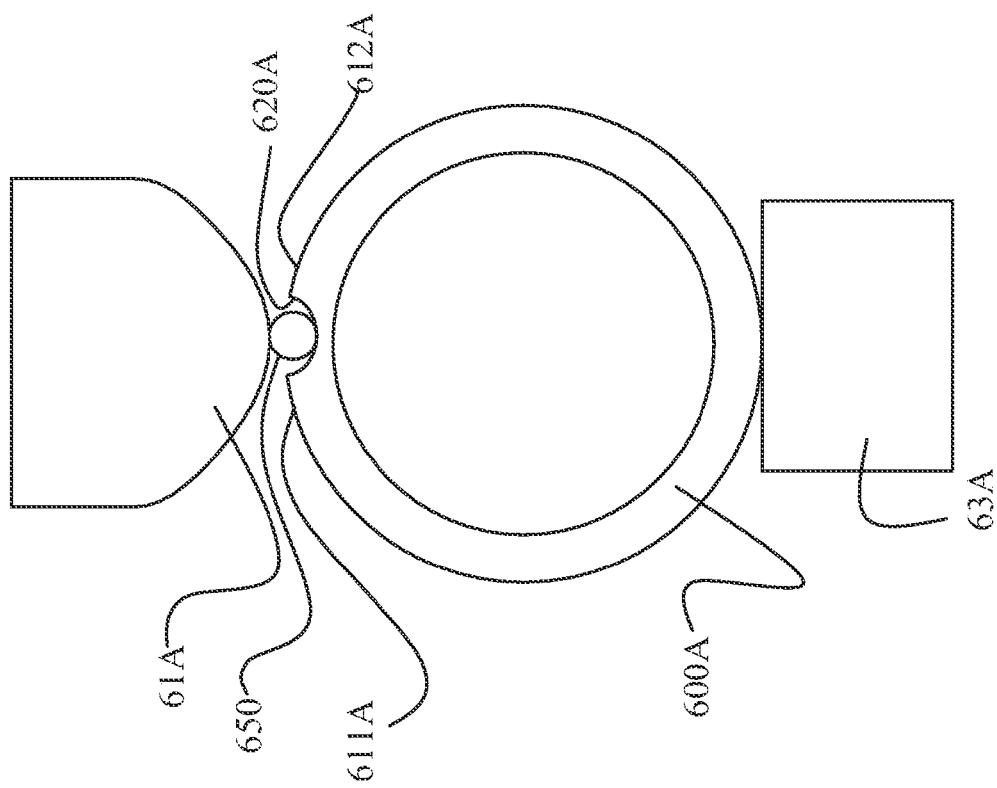

SEM VIEW OF EXEMPLARY WELDED JUNCTION

RESISTANCE WELDED JUNCTION FOR MEDICAL ELECTRICAL LEADS

TECHNICAL FIELD

The present invention relates to medical electrical leads and more particularly to welded junctions included in such leads.

BACKGROUND

Cardiac stimulation systems commonly include a pulse-generating device, such as a pacemaker or implantable cardioverter/defibrillator that is electrically connected to the heart by at least one electrical lead. An electrical lead delivers electrical pulses emitted by the pulse generator to the heart, stimulating the myocardial tissue via electrodes included on the lead. Furthermore, cardiac signals may be sensed by lead electrodes and conducted, via the lead, back to the device, which also monitors the electrical activity of the heart.

Medical electrical leads are typically constructed to have the lowest possible profile without compromising functional integrity, reliability and durability. Often junctions formed between a conductor and other components included in leads, for example electrodes, can increase the lead's profile, therefore it is desirable to develop low profile junctions.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIGS. 2A-B are perspective views of lead components according to alternate embodiments of the present invention;

FIGS. 6A-B are radial cross-sections of resistance welding setups according to alternate embodiments of the present invention;

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1:
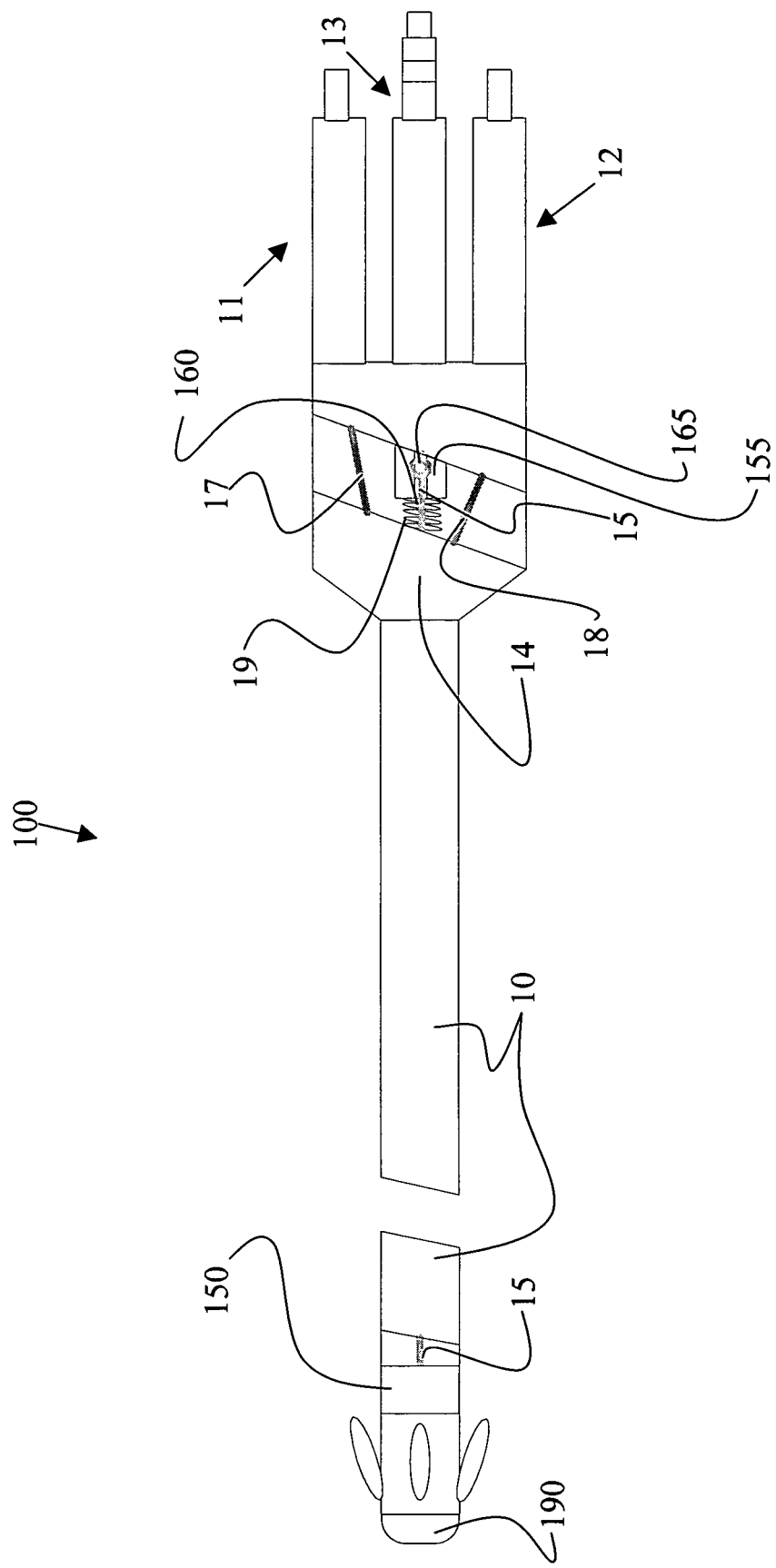
FIG. 1 is a plan view with partial sections of a lead according to one embodiment of the present invention.

FIG. 1 is a plan view with partial sections of a lead 100 according to one embodiment of the present invention. FIG. 1 illustrates lead 100 including a lead body to which two high voltage connector legs 11, 12 and one low voltage connector leg 13 are coupled via a transition sleeve 14; conductors 17, 18 and 19 extend from connector legs 11, 12 and 13, respectively, into lead body 10 where conductors 17 and 18 are coupled to defibrillation electrodes (not shown) and conductor 18 is coupled to a tip electrode 190. As is well known to those skilled in the art, connector legs 11, 12 and 13 are adapted to couple with a pulse generator for pacing and defibrillation therapy delivery.

FIG. 1 further illustrates lead 100 including a fourth conductor 15 coupled to an electrode ring 150 at a distal end and, at a proximal end, to a transition component 155 within sleeve 14 via a resistance weld 165; another conductor not shown is coupled to component 15 and extends within connector leg 13. According to embodiments of the present invention, and as is further illustrated in FIG. 2A, component 155 includes a groove 160 formed in an outer surface 250 into which cable 15 is positioned prior to resistance welding; an exemplary setup for such a weld is shown in FIG. 6A. Furthermore, electrode ring 150, as illustrated in FIG. 2B, includes a groove 220 formed in an inner surface 210 wherein the distal end of cable 15 is positioned for resistance welding according to embodiments of the present invention; an exemplary setup for this weld is illustrated in FIG. 6B. Grooves may extend along an entire length of a component or only along a portion of the length.

Figure 3:
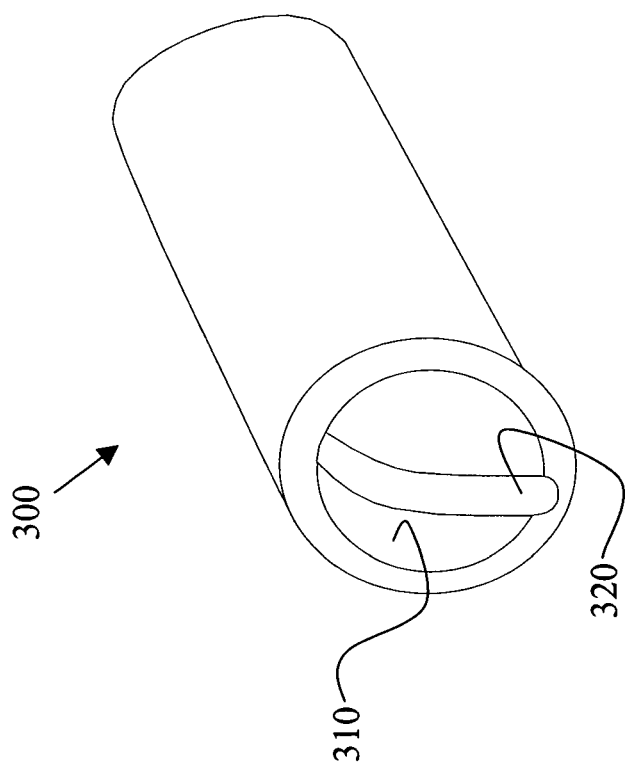
FIG. 3 is a perspective view of a component according to an alternate embodiment of the present invention.

Although FIGS. 2A-B illustrate grooves 220 and 160 extending approximately parallel with a longitudinal axis of the components 150 and 155, respectively, according to alternate embodiments, a groove may extend transversely from a longitudinal axis of a part, one example of which is shown in FIG. 3. FIG. 3 illustrates a component 300 including an inner surface 310 in which a spiral or helical groove 320 is formed; according to some embodiments such a groove accommodates a coiled wire conductor, for example coil conductor 18 illustrated in FIG. 1, a portion of which may be threaded or spun into groove 320.

Figure 4:
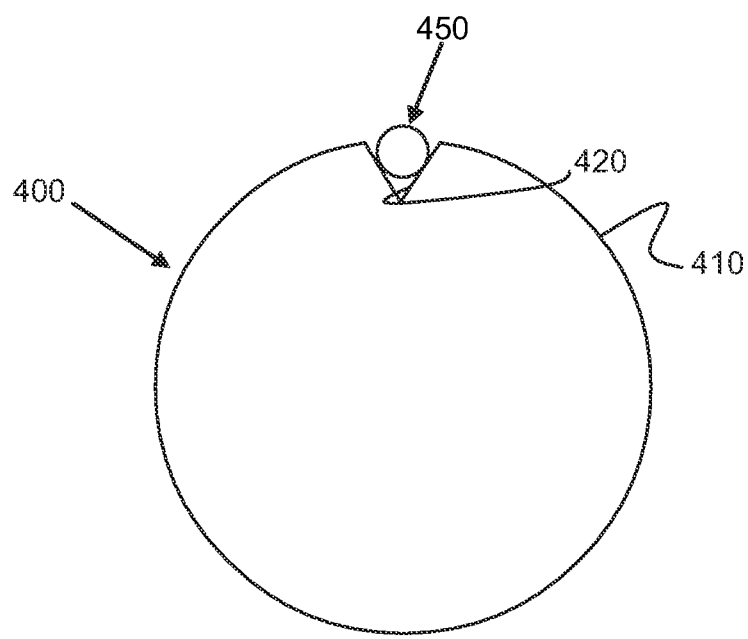
FIG. 4 is a radial cross-section of a pre-weld assembly according to another embodiment of the present invention.

FIG. 4 illustrates yet another embodiment of the present invention wherein a groove 420 formed in an outer surface 410 of a component 400 has a v-shaped cross-section as opposed to a semi-circular section of grooves 160, 220, and 320.

Figure 5:
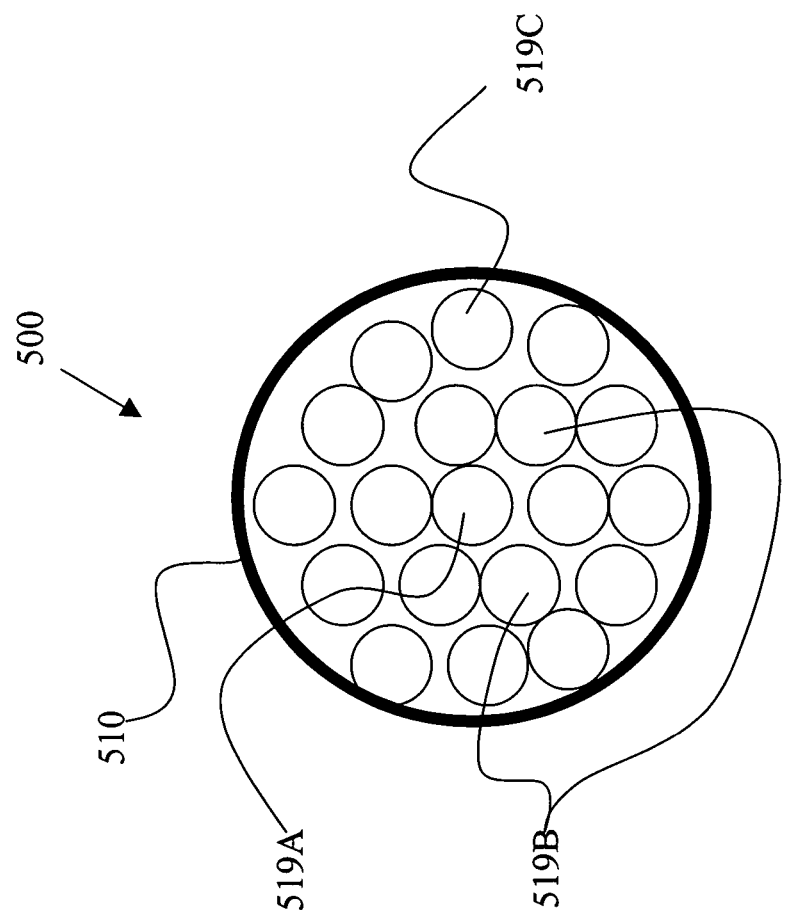
FIG. 5 is a radial cross-section of a conductor, which may be implemented in embodiments of the present invention.

FIG. 5 is a radial cross-section of a conductor 500, which may be implemented in embodiments of the present invention. FIG. 5 illustrates conductor 500 including nineteen wire strands 519A,B,C which have been cabled together and enclosed in an insulative outer sheath 510. According to an exemplary embodiment each strand 519A,B,C is formed of an MP35N alloy; a center strand 519A has a diameter of approximately 0.0014 inch, a left hand lay and a pitch of approximately 0.044 inch, intermediate peripheral strands 519B have a diameter of approximately 0.0013 inch and outer peripheral strands 519C have a diameter of approximately 0.0012 inch, both sets of peripheral strands 519B,C having a right hand lay and a pitch of approximately 0.038 inch. Outer sheath according to one set of embodiments is formed of a fluoropolymer material, for example PTFE or ETFE. Outer sheath 510 is stripped from a portion of cable 500 and that portion, is placed into a groove of a component for welding; according to embodiments of the present invention a diameter of cable 500 exceeds a depth of the mating groove.

Figure 6C:
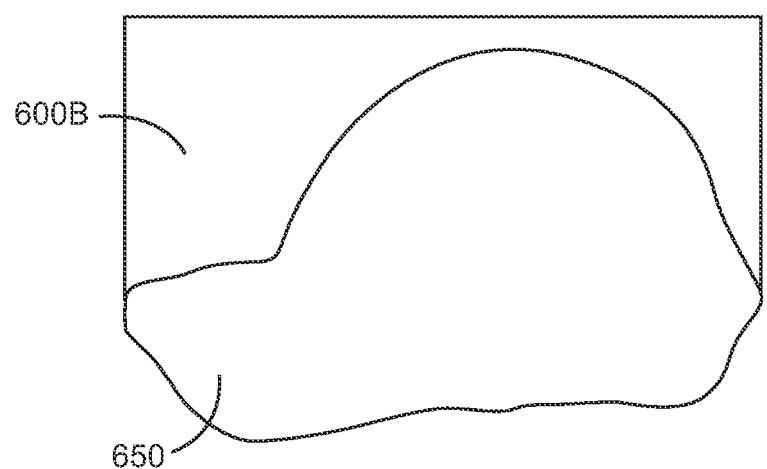
FIG. 6C is a scanning electron microscope (SEM) photograph of a section through a welded junction formed in accordance with the setup illustrated in FIG. 6B.

FIGS. 6A-B are radial cross-sections of resistance welding setups according to alternate embodiments of the present invention. FIGS. 6A-B illustrate a first welding electrode 61A,B and a second welding electrode 63A,B positioned on opposing sides in order to force a component 600A,B and a conductor 650 together while passing a current through component 600A,B and conductor 650 to generate enough heat to weld component 600A,B and conductor 650 together. FIGS. 6A-B further illustrate a diameter of conductor 650 exceeding a depth of a groove 620A,B in which conductor is positioned for welding; according to embodiments of the present invention, during the welding process, first electrode 61A,B is thus allowed to press cable 650 against surface of groove 620A,B, but is prevented from flattening cable 650, being stopped by surfaces 611A,B and 612A,B on either side of groove 620A, B. FIG. 6C is a scanning electron microscope (SEM) photograph of a section through a welded junction formed in accordance with the setup illustrated in FIG. 6B. Further details of a resistance welding technique will be described in an example included herein, furthermore, the fundamentals of resistance welding are well known to those skilled in the art.

EXAMPLE

A sample of weld junction assemblies were resistance welded using a Unitek UB25 Power Supply and a Unitek Series 61F Constant-force weld head in conjunction with the setup illustrated in FIG. 6B; each of the assemblies included a cable conductor, according to the exemplary embodiment described in conjunction with FIG. 5, and an electrode ring component, such as ring 150 illustrated in FIG. 2B. Referring now to FIG. 6B, first electrode 61B was formed of copper, included a molybdenum insert and had a diameter of approximately 0.063 inch; second electrode 63B was also formed of copper and included a rectangular molybdenum tip, approximately 0.030 inch by approximately 0.050 inch.

Referring back to FIG. 2B, the electrode ring used in these assemblies may be described in the context of ring 150 wherein a radius R of groove 220 was approximately 0.0035 inch and a wall thickness t at a base of groove 220 was approximately 0.004 inch. Each of the rings was formed from a 90/10 platinum iridium alloy and included a titanium nitride coating, being between approximately 2 and 10 microns thick, formed on their outer surfaces.

Figure 7:
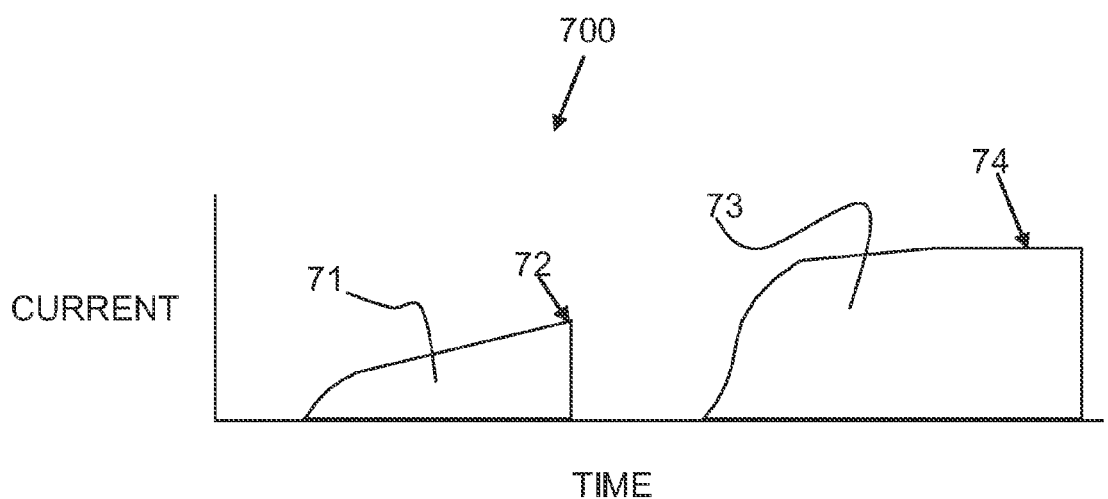
FIG. 7 is a plot of an exemplary welding process according to one embodiment of the present invention.

Table 1 includes pertinent welding parameters and FIG. 7 is a plot 700 of the welding process. FIG. 7 illustrates plot 700 of current, along an ordinate axis Y, versus time, plotted along an abscissa X, wherein current is initially applied in a pulse 71 to a peak pre-weld value 72, in order to condition each electrode ring component, and is then cut off and ramped up again in a weld pulse 73 to a peak weld value 74 where it is held to complete the welding process. Conditioning of the electrode ring components was included in the process due to the titanium nitride coating, which increases surface resistance of the components; since there is some variability in the thickness of the coating, weld quality could vary from part to part depending on coating thickness. Pre-weld pulse 71 is applied to 'blow away' a portion of the titanium nitride coating in order to normalize the resistance of the ring components so that a uniform weld pulse 73 applied to each assembly will result in uniform weld quality across the sample. Duration of pre-weld pulse 71 for this exemplary sample was approximately 20 milliseconds and peak pre-weld current 72 was approximately 400 amps, the time between pre-weld pulse 71 and weld pulse 73 was approximately 0.5 milliseconds and the duration of weld pulse 73 was approximately 3.5 milliseconds, with peak value 74 as indicated Table 1.

TABLE 1

| Welding parameters | | |
| --- | --- | --- |
| Sample # | Peak Weld Current (Amps) | Applied Force (lbs.) |
| 1 | 600 | 7 |
| 2 | 600 | 7 |
| 3 | 700 | 7 |
| 4 | 700 | 7 |
| 5 | 600 | 9 |
| 6 | 600 | 9 |
| 7 | 700 | 9 |
| 8 | 700 | 9 |

Each of the weld junction assemblies welded according to the process described by Table 1 and FIG. 7 were visually acceptable, in terms of an amount of expulsion from the cable within the melt pool and the degree to which the cable was compressed into the groove of the electrode, and exhibited sufficient strength in subsequent tensile-type testing.

In the foregoing detailed description, the invention has been described with reference to specific embodiments. However, it may be appreciated that various modifications and changes can be made without departing from the scope of the invention as set forth in the appended claims. For example, various combinations of conductors and components, in terms of material selection and overall component geometry may be included within the scope of the present invention; furthermore, resistance welding parameters, including welding electrode geometry, may be optimized by those skilled in the art according to material selection and component geometries.

What is claimed is:

1. A medical electrical lead, comprising:
   a component including a surface and a groove formed in the surface;
   a conductor, the conductor extending within the lead and including a plurality of wire strands cabled together positioned within the groove of the component; and
   a resistance weld formed between the conductor and the component;
   wherein the groove includes a depth and the conductor positioned within the groove includes a pre-weld diameter, the pre-weld diameter being greater than the depth of the groove.

2. The medical electrical lead of claim 1, wherein the surface has a curved profile.

3. The medical electrical lead of claim 2, wherein the component comprises a substantially tubular body and wherein the surface is an inner surface of the substantially tubular body.

4. The medical electrical lead of claim 2, wherein the surface of the component forms an outer diameter.

5. The medical electrical lead of claim 2, wherein the surface of the component forms an inner diameter and the component further includes an outer electrode surface.

6. The medical electrical lead of claim 5, wherein the outer electrode surface includes a titanium nitride coating.

7. The medical electrical lead of claim 2, wherein the groove spiraling about a portion of a circumference of the surface.

8. The medical electrical lead of claim 1, wherein the conductor is a coil.

9. The medical electrical lead of claim 1, wherein the groove extends approximately aligned with a longitudinal axis of the component.

10. The medical electrical lead of claim 1, wherein the groove extends approximately transverse to a longitudinal axis of the component.

11. The medical electrical lead of claim 1, wherein the groove includes an approximately semi-circular cross-section.

12. The medical electrical lead of claim 1, wherein the groove includes an approximately v-shaped cross-section.

13. The medical electrical lead of claim 1, wherein the component comprises an elongated body, and wherein the groove comprises a longitudinal slot substantially parallel with the longitudinal axis of the elongated body.

14. A medical electrical lead, comprising:
- a component comprising a substantially tubular body having an inner surface and a groove formed in the inner surface;
- a conductor comprising a plurality of wire strands cabled together, the conductor extending within the lead and positioned within the groove of the component; and
- a resistance weld formed between the conductor and the component;
- wherein the groove includes a depth and the conductor positioned within the groove includes a pre-weld diameter, the pre-weld diameter being greater than the depth of the groove.

* * * * *